(12) United States Patent
Snell

(10) Patent No.: US 6,732,735 B1
(45) Date of Patent: May 11, 2004

(54) RETICULATED COATINGS

(75) Inventor: Robert Snell, Newmarket (GB)

(73) Assignee: Ranier Limited, Fountain House, Cambridge (GB)

( * ) Notice: Subject to any disclaimer, the term of this patent is extended or adjusted under 35 U.S.C. 154(b) by 0 days.

(21) Appl. No.: 09/555,230

(22) PCT Filed: Nov. 26, 1998

(86) PCT No.: PCT/GB98/03547

§ 371 (c)(1),
(2), (4) Date: May 26, 2000

(87) PCT Pub. No.: WO99/26665

PCT Pub. Date: Jun. 3, 1999

(30) Foreign Application Priority Data

Nov. 26, 1997 (GB) .............................................. 9725031

(51) Int. Cl.⁷ .................................................. A61F 6/04
(52) U.S. Cl. ....................................... 128/844; 128/918
(58) Field of Search ................................ 128/842, 844, 128/918; 604/347–353

(56) References Cited

U.S. PATENT DOCUMENTS

| 4,135,011 | A | * | 1/1979 | Mimura ....................... 427/246 |
| 4,371,636 | A |   | 2/1983 | Distler et al. |
| 4,729,914 | A |   | 3/1988 | Kliment et al. |
| 5,686,012 | A | * | 11/1997 | Hayashi ................... 252/62.56 |
| 5,799,978 | A | * | 9/1998 | Grinnell ....................... 281/29 |
| 6,207,738 | B1 | * | 3/2001 | Zuckerman ................. 524/156 |

FOREIGN PATENT DOCUMENTS

| GB | 960.508 | 6/1964 |
| GB | 970682 | 9/1964 |
| GB | 1052546 | 12/1966 |
| GB | 1167670 | 10/1969 |
| GB | 1 435 821 | 5/1976 |
| GB | 1 600 963 | 10/1981 |

* cited by examiner

Primary Examiner—Michael A. Brown

(57) ABSTRACT

A method of forming a reticulated coating on a substrate includes providing an agglomerate dispersion of a first polymer in a polar liquid carrier on a surface of the substrate, and evaporating the liquid carrier to form the coating.

50 Claims, 16 Drawing Sheets

100 µm

25 µm

100 μm

25 μm

100 μm

25 μm

100 μm

25 μm

100 μm

25 μm

PVC COATING (NO WASH)

HEC COATED

HEC COATED

PVP WITH NaCl PARTICLES

HEC COATED

HEC COATED POLYMER

RETICULATED COATINGS

BACKGROUND OF THE INVENTION

1. Field of the Invention

The present invention relates to reticulated coatings and, in particular, to reticulated coatings that exhibit enhanced lubricity or "slip" with respect to both dry and damp surfaces and are suitable for use in medical device products.

2. Description of the Related Art

Thin polymer films are used in the manufacture of a variety of medical device products, such as medical gloves, condoms, wound dressings, catheters, angioplasty balloons and the like. In the case of medical gloves, such as surgeon's gloves or examination gloves, the ease of donning the glove is an important consideration, as too is the breathability of the base polymer, to reduce the build-up of moisture within the glove. Consequently, such gloves usually require the application of powders or coatings which confer anti-frictional properties. Ultimately, however, the barrier properties of gloves and condoms are of primary concern and it is essential that the application of any coating should not reduce these properties. An additional requirement of such a coating is that it must adhere strongly to the underlying substrate and must be able to be applied to a variety of substrate materials without degrading the intrinsic properties of the substrate material. Soft elastomeric films are of particular value as coatings (and also as "film articles", such as condoms) but are characterised by the tacky or "blocky" nature of the film surfaces when dry, which can lead to problems of unwanted adhesion when products are stored or dried in bulk. In order to overcome this, products are frequently treated with a dusting powder, such as corn starch, to render the surface tack-free. However, post-operative adhesions and granulomas have become increasingly associated with the presence of such powders on invasive medical devices, whilst undesirable allergic hypersensitivity reactions to latex used in medical gloves may be exacerbated by the presence of such powders. Consequently, the alternative of using a powder free, anti-block coating to prevent adhesion and confer slip properties has particular value.

U.S. Pat. No. 4,642,267, for example, discloses a hydrophilic blend comprising an organic solvent-soluble, thermoplastic polyurethane and a hydrophilic poly(N-vinyl lactam) which is slippery in aqueous environments and may be used as a low-friction coating for catheters. The blend is prepared using conventional melt-blending techniques or by dissolving the components in a solvent, which is subsequently evaporated to yield the blend. In the latter case, however, this document discloses that the solvent must be capable of dissolving both polymer components in a single-phase solution and that the relative volatilities must be such that, at no point during evaporation and drying, must the solution tend to precipitate either polyurethane or poly(N-vinyl lactam) or an association complex of these polymers which may have different solubility characteristics than either material by itself.

Anti-block coatings prepared by conventional methods often require elaborate and expensive manufacturing procedures and the properties of the coatings so obtained are often inferior to those of dusting powders. It is an object of the present invention to overcome some of the aforementioned disadvantages by providing a novel method of forming a reticulated coating that has good "slip" properties when damp or dry.

SUMMARY OF THE INVENTION

Accordingly, in a first aspect of the invention, there is provided a method of forming a reticulated coating on a substrate, comprising providing an agglomerate dispersion of a pre-formed first polymer in a polar liquid carrier on a surface of the substrate, and evaporating the liquid carrier to form the coating.

In one embodiment, the reticulated coating is adapted to render the surface of the substrate substantially tack-free or anti-blocking when dry, so as to ensure that articles that are provided with the coating, such as medical gloves, do not adhere to each other. Preferably, the reticulated coating is substantially free of substances capable of causing undesirable allergic hypersensitivity reactions, which is particularly important if the coatings are to be used for medical applications. In another embodiment, the coating has an Ra value of at least 0.5 $\mu$M.

In the context of the present invention, the term "$R_a$ value" is understood to refer to the arithmetic mean of the absolute departures of the roughness profile of the surface from the mean line, in accordance with its usual meaning in relation to engineering surfaces (see, for example, ISO 4287/1:1997, and also ISO 11 562). Similarly, $R_q$ or RMS is the root mean square parameter corresponding to $R_a$, whilst $R_{max}$ is the maximum peak to valley height of the profile in the assessment length. The first polymer may be any material capable of forming a film coating when wet but is generally a thermoplastic, a thermosetting resin or an elastomer and will already have been polymerized before it is used to prepare the agglomerate dispersion, i.e., the agglomerate dispersion will not usually be obtained as the product of an in situ polymerization reaction. Preferably, the thermoplastic, thermosetting resin or elastomer is selected from the group consisting of polythene, polypropene, polymethylpentane, polystyrene, polyvinyl chloride, polyvinyl acetate, polyvinyl alcohol, polymethyl methacrylate, polyacrylonitrile, polyacrylamide, aromatic polyesters, polycarbonates, polyamines, polytetrafluoroethene, alkyd resins, unsaturated polyesters, urea-methanal polymers, polyureas, melamines, polyurethanes, polyamides, epoxy resins, polyethene oxide, polyphenylene oxide, polyacetals, polyaldehydes, phenolic resins, polysulphones, natural rubbers, polyisoprene, polybutadiene, polychloroprenes, butyl rubbers, styrene-butadiene rubbers, acrylonitrile-butadiene rubbers, polysulphides, silicones and mixtures thereof. In the context of the invention, the phrase "mixtures thereof" should be understood to include co-polymers of any of the preferred monomers, as well as simple mixtures of the fully polymerised compounds. It is especially preferred that the thermoplastic, thermosetting resin or elastomer is selected from the group consisting of polyurethanes, neoprene, latex, styrene acrylic emulsions and nitriles. Most preferably, the first polymer is a polyurethane or a natural rubber, such as latex. Polyurethanes are especially preferred, particularly those prepared from polyesterpolyols, polyetherpolyols, polycarbonatepolyols and mixtures of these. The polar liquid carrier may be any liquid carrier capable of developing an electrical charge and forming an agglomerated dispersion with the first polymer. Such liquid carriers may include but are not limited to water, dilute mineral acids, methanol, ethanol, diethylether, dimethylsulphoxide and dimethylsulphone. Preferably, the liquid carrier is aqueous. In one embodiment, the agglomerated dispersion of the first polymer is applied to the surface of the substrate after it has been formed, preferably by spraying the agglomerated dispersion onto the substrate or by dipping the substrate in the agglomerated dispersion. In an alternative embodiment, the agglomerate dispersion is formed in situ on the surface of the substrate, preferably by applying a colloidal dispersion of the first polymer to the surface of the substrate and by inducing agglomeration, for example, by electrolysis. In a preferred embodiment, the agglomerate dispersion of the first polymer is formed from a colloidal dispersion of the first polymer in the polar liquid carrier. In this embodiment, the colloidal dispersion preferably contains micelles of the first polymer having an average particle size in the range of 0.1–100 nm, preferably 1–75 nm, and especially about 50 nm.

Preferably, the reticulated coating is lubricious and confers enhanced slip with respect to both dry and damp surfaces. In any of these embodiments, the average size of the particles in the agglomerated phase may be in the range of 0.1–100 µm, preferably 0.5–25 µm, most preferably 1–15 µm. In a preferred embodiment, the agglomerate dispersion may also comprise a second polymer, preferably preformed. The second polymer may be any compound that confers suitable properties on the final coating but will generally be selected from the group consisting of polyolefins, polyamines, polyamides, polysaccharides, polyamino sugars, polynucleotides, phospholipids and mixtures thereof. In an embodiment, the second polymer is capable of interacting with the polar liquid carrier in such a way that the first polymer is induced to form an agglomerate dispersion in the polar liquid carrier. For example, the second polymer may be capable of forming an intimate network with the polar liquid carrier, such as a hydrogel or a colloidal solution, thereby reducing the ability of the polar liquid carrier to interact with the first polymer and causing the first polymer to form an agglomerate dispersion in the polar liquid carrier. Preferably, the second polymer forms a colloidal suspension with the polar liquid carrier. In another embodiment, the polar liquid carrier is aqueous and is capable of hydrogen bonding with the second polymer, such that the free energy of the polar liquid carrier is reduced, thereby increasing the tendency of (possibly micelles of) the first polymer to agglomerate.

Preferably, the second polymer is selected from the group consisting of poly(aromatic alkenes), poly(meth)acrylates, glucosamine-containing polymers, galactosamine-containing polymers, alginates, pectins, polypeptides, poly (N-vinyl lactams), cellulose, cellulose derivatives, lecithins, cephalins, sphingomyelins and mixtures thereof. Most preferably, the second polymer is soluble in water and is selected from the group consisting of polystyrene, polymethyl methacrylate, polyvinylpyrrolidone, poly(N-vinyl caprolactam), hydroxymethylcellulose, hydroxyethylcellulose, pectin esterified from citrus fruit, sodium alginates, chitosan, chitin, poly(N-acetyl-D-glucosamine), co-polymers of polyvinylpyrrolidone with 2-dimethylaminoethylmethacrylate, co-polymers of polyvinylpyrrolidone with styrene, co-polymers of polyvinylpyrrolidone with acrylic acid, polyethylenimine, ethoxylated polyethylenimines, N-propionyl substituted linear polyethylenimines, 1-[N[poly(3-allyloxy-2-hydroxypropyl)]-2-aminoethyl]-2-imidazolidinone, polyacrylamides, co-polymers of polyacrylamide with acrylic acid, poly(2-ethyl-2-oxazoline), L-α-phosphatidylcholine dioctanoyl, and mixtures thereof. Polyvinylpyrrolidone and hydroxyethylcellulose are especially preferred, as the use of these components produces coatings with excellent but quite distinct surface characteristics and properties.

The agglomerate dispersion may be formed by any suitable method but will generally be formed in the presence of an electrolyte, such as a salt. In this embodiment, the salt is preferably a metal salt or an ammonium salt selected from the group consisting of fluorides, chlorides, bromides, sulphates, sulphites, sulphides, hydrogencarbonates, carbonates, nitrates, nitrites and mixtures thereof. Of these, sodium chloride is especially preferred, although many other salts, such as lithium chloride or calcium chloride, may be equally effective. The salt may be present in any amount effective to induce agglomeration of the first polymer but is preferably present in an amount of from 0.01 g/l to 100 g/l, particularly 0.05 g/l to 50 g/l, more preferably 0.1 g/l to 10 g/l, and especially 6.0 g/l, based on the total volume of the agglomerate dispersion. Optionally, the agglomerate dispersion may also be formed in the presence of a surfactant, especially one which helps to solubilize the first polymer or helps to disperse the first polymer throughout the solution. Surfactants suitable for this purpose may be any amphoteric, ionic, cationic and non-ionic surfactants that are suitable for use on skin and other tissues and include but are not limited to long-chain fatty acids, quaternary ammonium compounds, betaines and suteines, amine oxides, sulfosuccinates and isothionates. Preferably, the surfactants are selected from the group consisting of alkyldimethylammonium betaines, coco aminopropyl betaine, N-lauryl or N-cetyl pyridinium salts, hydroxyethylheptadecenylimidazoline salts, hexadecyltrimethylammonium chloride, benzalkonium chloride and hexadecyl pyridinium chloride. In a preferred embodiment, an aqueous colloidal dispersion of the first polymer is added to an aqueous salt solution containing the second polymer dissolved therein. In this case, the colloidal dispersion contains micelles of the first polymer component having an average particle size in the range of 0.1–100 nm, preferably in the range of 1–75 nm, and especially about 50 nm.

In an embodiment of the invention in its first aspect, the coated substrate is washed after the liquid carrier has been evaporated so as to remove unwanted residues, such as salt used to form the agglomerate dispersion. Depending upon the nature of the second polymer however, the washing step may also remove substantially all of the second polymer from the coating itself. This is especially noted where the second polymer is hydroxyethylcellulose. Alternatively, the second polymer may be substantially undissolved by the washing step and remains present in the coating, as observed when the second polymer comprises polyvinylpyrrolidone. In an especially preferred embodiment of the invention, a third polymer is applied to the surface of the substrate, preferably as a film or thin layer, prior to providing the agglomerate dispersion. The third polymer may comprise a thermoplastic, a thermosetting resin or an elastomer, such as those used for the first polymer and, preferably, the third polymer is the same as the first polymer. The third polymer may be applied to the surface of the substrate in the form of a solution or a suspension, possibly by dip-coating or by spraying, and may be dried before the agglomerate dispersion is provided on the surface. Preferably, the third polymer is dried at a temperature of 15–150° C. for a period of 1–60 minutes, more preferably at a temperature of 50–100° C. for a period of 1–30 minutes, and especially at a temperature of about 80° C. for a period of about 5–10 minutes. However, the exact temperature and duration of the drying step required to give good coating characteristics may be determined by routine experimentation. It has been observed that, depending upon the drying time and the degree of "wetness" of the film of the third polymer the agglomerate dispersion of the first polymer interacts with the surface of the substrate to a greater or lesser degree giving markedly different properties to the final product. The precise mechanism by which this occurs is not fully understood but is believed to be determined by the hydrophilic/hydrophobic nature of the third polymer, as well as the potential for hydrogen bonding. In a further embodiment, the reticulated surface of the coated substrate is treated with a surfactant to further increase the damp slip properties of the substrate. Surfactants suitable for this purpose may be any amphoteric, ionic, cationic and non-ionic surfactants that are suitable for use on skin and other tissues and include but are not limited to long-chain fatty acids, quaternary ammonium compounds, betaines and suteines, amine oxides, sulfosuccinates and isothionates. Preferably, the surfactants are selected from the group consisting of alkyldimethylammonium betaines, coco aminopropyl betaine, N-lauryl or N-cetyl pyridinium salts, hydroxyethylheptadecenylimidazoline salts, hexadecyltrimethylammonium chloride, benzalkonium chloride, hexadecyl pyridinium chloride and silicones/organosiloxane polymers.

In a second aspect of the invention, there is provided a reticulated coating obtained by a method according to the invention in its first aspect. Preferably, the coating so obtained is reticulated or "roughened" and has a reticulated component particle size in the range of 1–25 μm and an average roughness in the range of 1–10 μm, preferably in the range of 2–12 μm with an average roughness of about 5 μm.

In a third aspect of the invention, there is provided an article having a reticulated coating according to the invention in its second aspect. Preferably, the article is a medical device, such as a condom, a medical glove, a wound-dressing, a catheter, an angioplasty balloon, a stent, a valve, or a surgical suture.

Thus, the present invention provides an anti-block coating system which may be applied to a variety of substrate materials, including glass, metal, ceramics, PVC, natural rubber latex, polyurethane, nylon, polyethylene and mixtures or composites of any of these. Such anti-block coatings can be applied to a medical device, such as a surgeon's glove, by applying a thin layer of the agglomerated dispersion onto the device, by for example spraying or dipping, and then heating the device in an oven to drive off the aqueous component of the coating system. This results in a multitude of agglomerate particles adhered onto the medical device surface. The adhered agglomerates may be conjoined to form a continuous but reticulated surface, alternatively the agglomerates may form a discontinuous coating with uncoated areas of substrate. The continuity of the coating, the size of the agglomerates and the resulting roughness of the reticulated surface may be manipulated within certain limits in order to modify the anti-block properties and lubricity of the coating. Furthermore, the formulation of the coating system may be modified to give agglomerates with a range of morphologies exhibiting different adherence, anti-block and lubricity properties.

DESCRIPTION OF THE PREFERRED EMBODIMENTS

Figure 1:
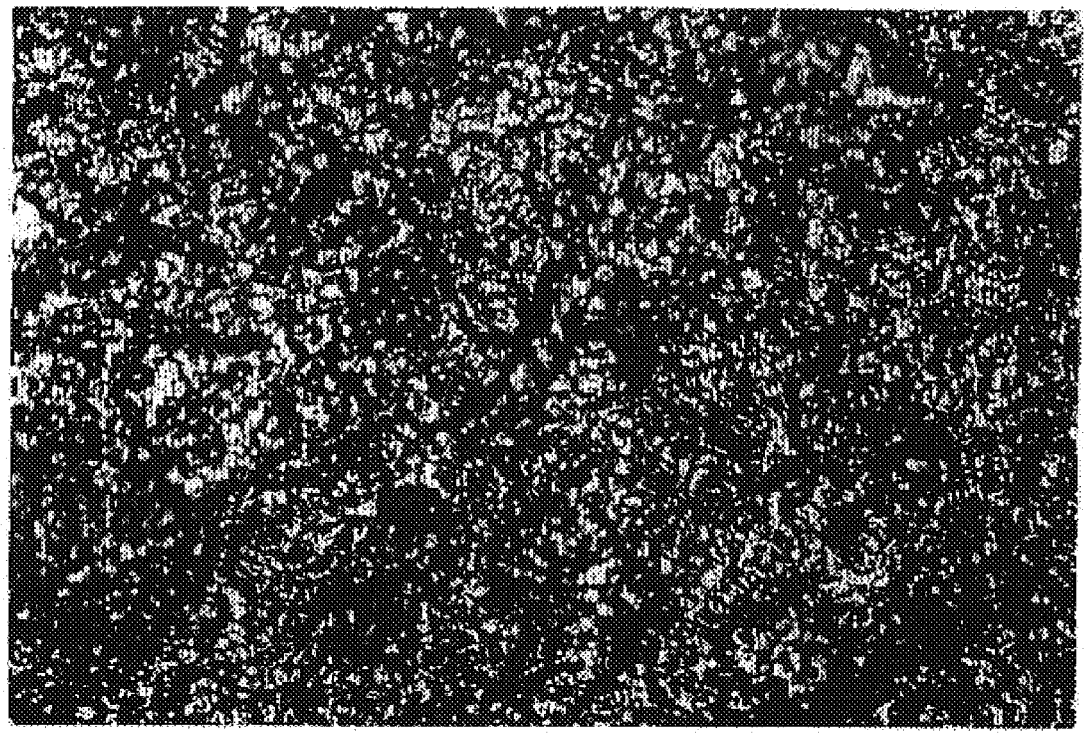
FIG. 1 shows a reflected light differential interference contrast micrograph of reticulated surface RET-001 using a 10× objective set for optimum contrast.

In order that the invention may be better understood, it will now be described in greater detail, by way of illustration only, with reference to the following specific examples.

Typically, an aqueous polyurethane is added to an ionic (salt) suspension containing PVP (polyvinylpyrrolidone) or HEC (hydroxyethylcellulose). Products requiring the addition of a reticulated coating may be dipped in the above solution and dried for a defined time and temperature. Following this procedure, a reticulated coating is formed on the surface of the product. Such coatings may be applied, for example, to polyurethane (both aqueous and solvent based) and latex substrates. The morphology of the reticulated coating can be modified through composition and processing conditions to give a range of surface properties. Changing the second phase from PVP to HEC has a dramatic effect on both the surface chemistry and the surface morphology. The coating changes from an agglomerated texture with PVP (i.e., where the reticulated component forms in well defined regions) to a well dispersed phase in the case of HEC. In the latter there is a broad distribution in particle size of the reticulated component. For the PVP coating, the peak to valley height is 12 $\mu$m and the average, roughness, $R_a$, is 5 $\mu$m. For the HEC coating, the peak to valley height is 8 $\mu$m and the average roughness is 1.5 $\mu$m. The reticulated surface can be made discrete (as with HEC) or conjoint (as with PVP). This relates to the compatibility of the second phase with the polyurethane, as well as the process conditions. It has been found that HEC is incompatible with the polyurethane such that no HEC is present in the final reticulated coating. On the other hand, PVP is bound within the final reticulated coating as well as coating the base urethane. The nature of this interaction appears to be associated with hydrogen bonding. It can be shown that the two systems described behave differently. Transmission electron microscopy reveals the normal micelle structure of polyurethanes in aqueous suspension to be of the order of 50 nm. Given the size of the agglomerates and their morphology from optical, scanning and atomic force microscopy, the addition of a second phase, plus the use of an ionic salt solution, would appear to transform the dispersed micelles into a colloidal suspension wherein the coalesced particles deposited onto the substrate are of the order of 2 to 10 $\mu$m.

It would seem, therefore, that a dynamic equilibrium is set up between the aqueous phase, the ions in solution and the two or more polymers, which is highly dependent upon temperature, pH, viscosity and concentration of each component. An additional consideration is the nature of the substrate to be coated with the reticulated coating. The hydrophobic/hydrophilic characteristics, as well as the surface energy of the material, will determine the wetting properties and hence the morphology of the reticulated coating. For example, altering the drying time of the substrate changes the amount of water available at the surface; as a polyurethane film dries, the surface tends to become more hydrophobic. The surface energy of the material would therefore increase, giving rise to a greater contact angle between the substrate and the aqueous coating solution. A particular property of polyurethanes, which is relevant to this process, is hydrogen bonding. Inter-chain coupling occurs between oxygen and hydrogen. This attraction between neighbouring chains is an important property in polyurethanes and partly accounts for the tackiness exhibited by polyurethane surfaces, especially when two free surfaces come into contact with each other. Polyurethanes are adaptive polymers containing both hydrophilic and hydrophobic functionality. The presence of water at the surface of a polyurethane film will result in an instantaneous re-orientation of functional groups at the surface, thus lowering the surface free energy. The hydrophobic groups re-orientate themselves away from the aqueous phase. With extended contact, diffusion of water occurs into the polymer, aided by the hydrophilic phase. The typical equilibrium water content under normal atmospheric conditions is 1%, which can rise to several percent when in contact with water for an extended period of time. The polymer in this case undergoes internal re-orientation such that hydrophobic and hydrophilic domains may be created. Another factor controlling both mechanical and surface properties is domain ordering. Polyurethanes exist as two phase materials such that they have hard and soft block domains. With time, the hard blocks coalesce resulting in increased ordering of the polymer. The ordered phase is temperature dependent, and therefore changes in temperature result in a time dependent re-orientation of the polymer. One final factor that needs to be considered when attempting to understand surface properties is the role of the substrate (e.g., whether a metal, glass, ceramic, etc.). For thin coatings, there will be an influence from the substrate upon the final surface chemistry. The mechanism of this is not well understood but is related to the nature of the interaction between the substrate and the solution.

EXAMPLE 1

Preparation and Properties of Sample Coatings

In order to compare the effects of these various parameters, the following samples of polyurethane coatings were prepared in accordance with the invention:

RET-001 Sample prepared on a glass substrate using a base of a commercially available elastomeric aliphatic polyester polyurethane subsequently coated with Sancure® 2255 polyurethane with 20 weight % PVP and sodium chloride addition (6 g/l). The sample was dried for 5 minutes at 80° C. between coats. A final 10 minute wash was used. Film thickness: 50 $\mu$m. [N.B. Polyurethane starting materials were obtained from B F Goodrich (UK) Ltd., Swan House, 203 Swan Road, Hanworth, Middlesex TW13 6LL.]

RET-002 Sample prepared on a glass substrate using a base of a commercially available elastomeric aliphatic polyester polyurethane subsequently coated with Sancure® 2255 polyurethane with 20 weight % PVP and sodium chloride addition (6 g/l). The sample was dried for 10 minutes at 80° C. between coats. A final 10 minute wash was used. Film thickness: 50 $\mu$m.

RET-003 Sample prepared on a probe cover former using a base of a commercially available elastomeric aliphatic polyester polyurethane with Sancure® 2255 polyurethane with 20 weight % PVP and sodium chloride addition (6 g/l). The sample was dried for 10 minutes at 80° C. between coats. A final 10 minute wash was used. Film thickness: 50 $\mu$m.

RET-004 Sample prepared on a glass substrate using a base of a commercially available elastomeric aliphatic polyester polyurethane with Sancure® 2255 polyurethane with 20 weight % PVP and sodium chloride addition (6 g/l). The sample was dried for 10 minutes at 80° C. between coats. No final wash was given to the material. Film thickness: 60 $\mu$m.

RET-005 Sample prepared on a glass substrate using a base of a commercially available elastomeric aliphatic polyester polyurethane with Sancure® 2255 polyurethane with 20 weight % HEC and sodium chloride addition (6 g/l). The sample was dried for 10 minutes at 80° C. between coats. No final wash was given to the material. Film thickness: 55 $\mu$m
Surface Analysis of Sample Products.

A wide range of analytical techniques were used to enable the surface morphology and chemistry of the samples to be characterized. It has to be recognised that the techniques in themselves need to be as non-destructive as possible. For example, the use of environmental scanning electron microscopy has to be preferred because there is no need to coat the sample and vacuum is not required.
Reflected Light Differential Interference Contrast (DIC) Microscopy.

Samples for DIC were first coated with a thin (200 nm) layer of gold to enhance the reflectivity of the substrate.

Images were obtained using a 10× and 40× objective set for optimum contrast. Images were obtained for RET-001, 002, 003, 004 and 005 and are shown in FIGS. 1 through 10. In the case of RET-001 and RET-002, the effect of drying time on the final morphology is dramatic. Doubling the drying time from 5 minutes to 10 minutes results in a two phase microstructure. The reticulated component appears to form a conjoint phase with the base polymer forming the matrix. In contrast, the two phases cannot be easily identified when a reduced drying time has been utilised. The effect is clearly related to the drying behaviour of the base polymer film, i.e., the residual water content will determine the wetting characteristics upon the application of the reticulated coating. DIC of RET-004 reveals a morphology similar to that observed previously. Application of the reticulated coating to a probe cover former, changes the morphology (RET-003, FIGS. 5 and 6). The reticulated coating forms a conjoint phase with the base polymer. Differences in morphology may be attributed to the base polymer film being thinner than other samples prepared, and therefore there may be an influence from the substrate material. The addition of HEC to Sancure® 2255 (RET-005) appears to change significantly the morphology of the polyurethane in comparison to that produced by the addition of PVP. The HEC coating produces a reticulated surface that is predominantly spherical in nature with a broad range of particle sizes observed.

Figure 2:
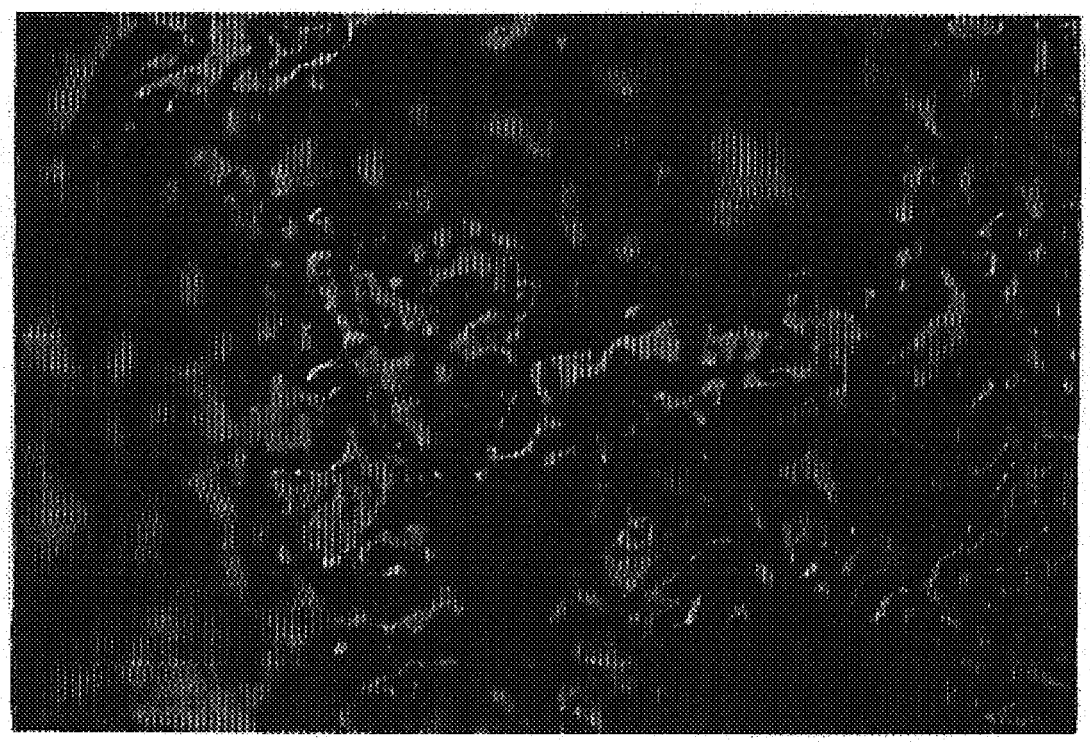
FIG. 2 shows a reflected light differential interference contrast micrograph of reticulated surface RET-001 using a 40× objective set for optimum contrast.
Figure 3:
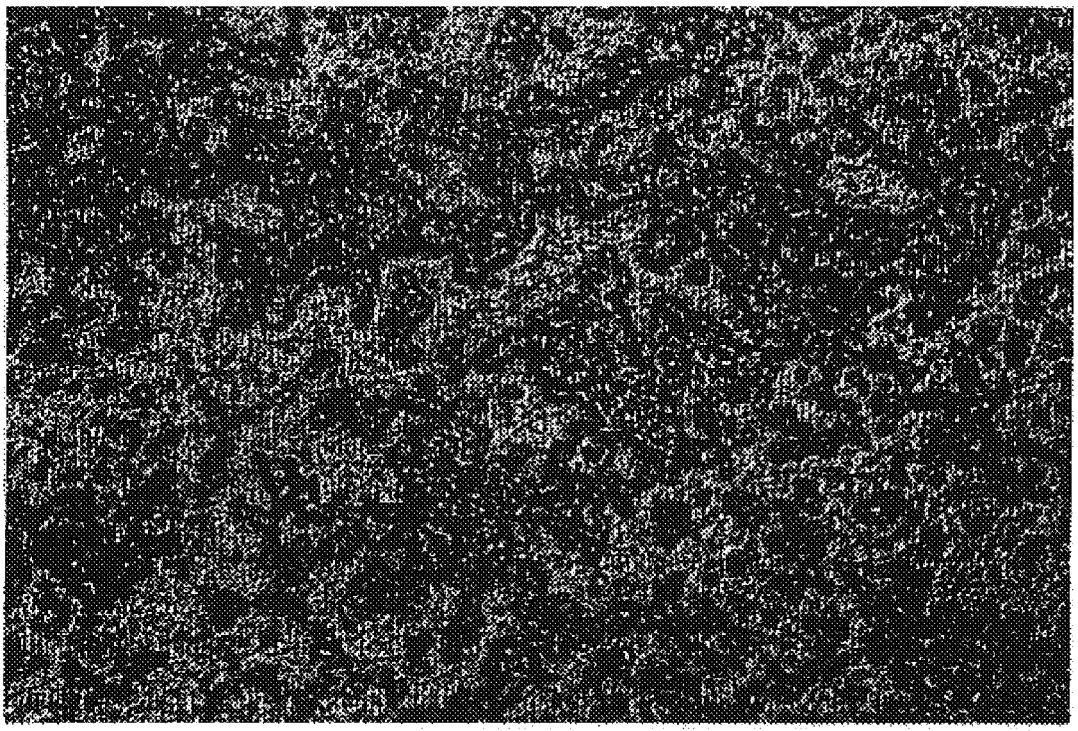
FIG. 3 shows a reflected light differential interference contrast micrograph of reticulated surface RET-002 using a 10× objective set for optimum contrast.
Figure 4:
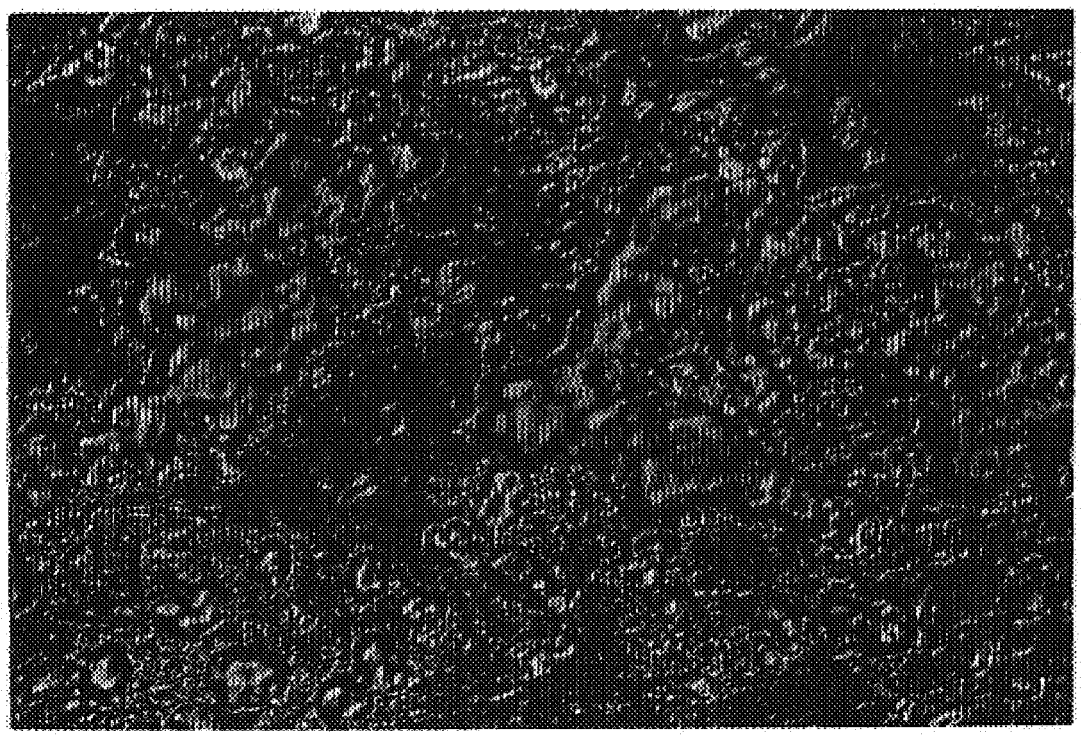
FIG. 4 shows a reflected light differential interference contrast micrograph of reticulated surface RET-002 using a 40× objective set for optimum contrast.
Figure 5:
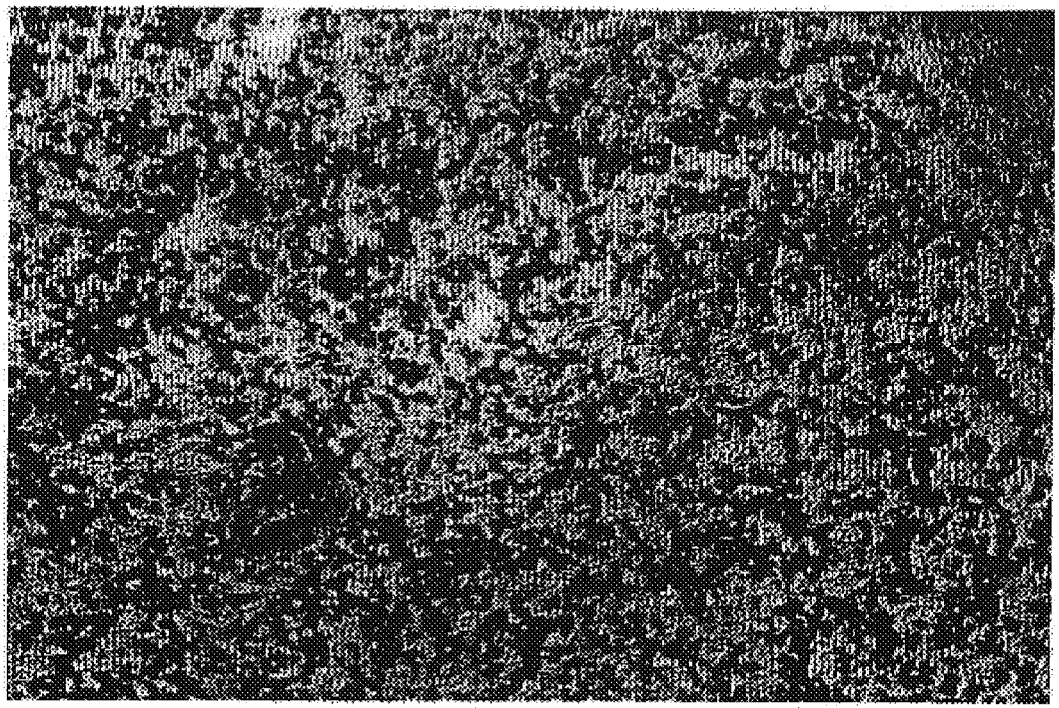
FIG. 5 shows a reflected light differential interference contrast micrograph of reticulated surface RET-003 using a 10× objective set for optimum contrast.
Figure 6:
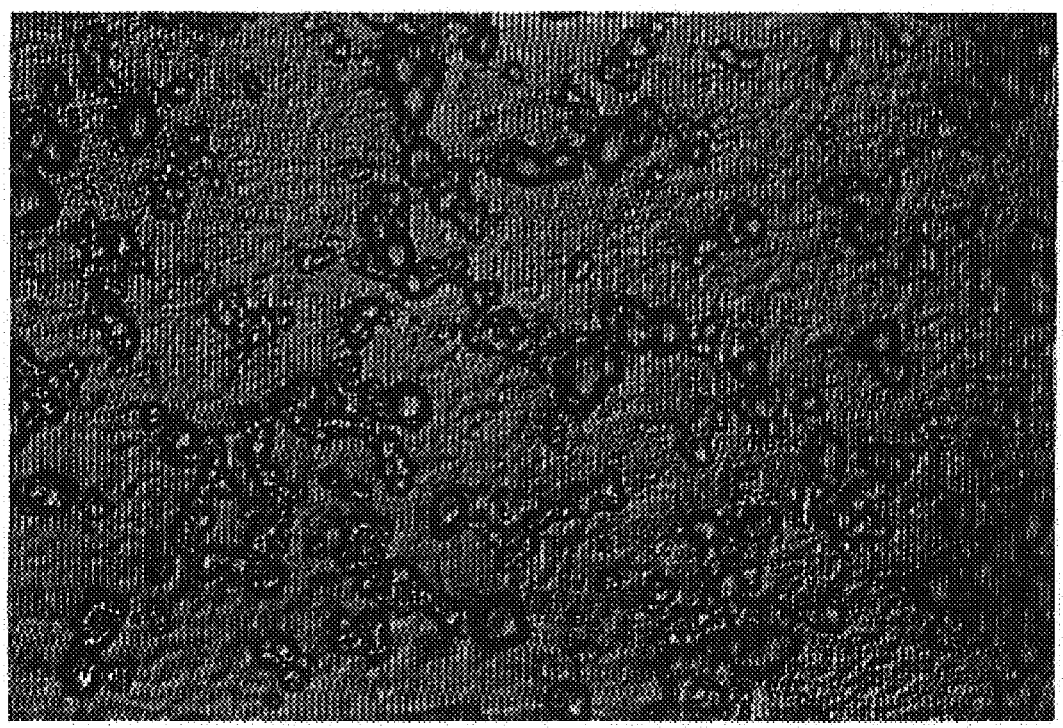
FIG. 6 shows a reflected light differential interference contrast micrograph of reticulated surface RET-003 using a 40× objective set for optimum contrast.
Figure 7:
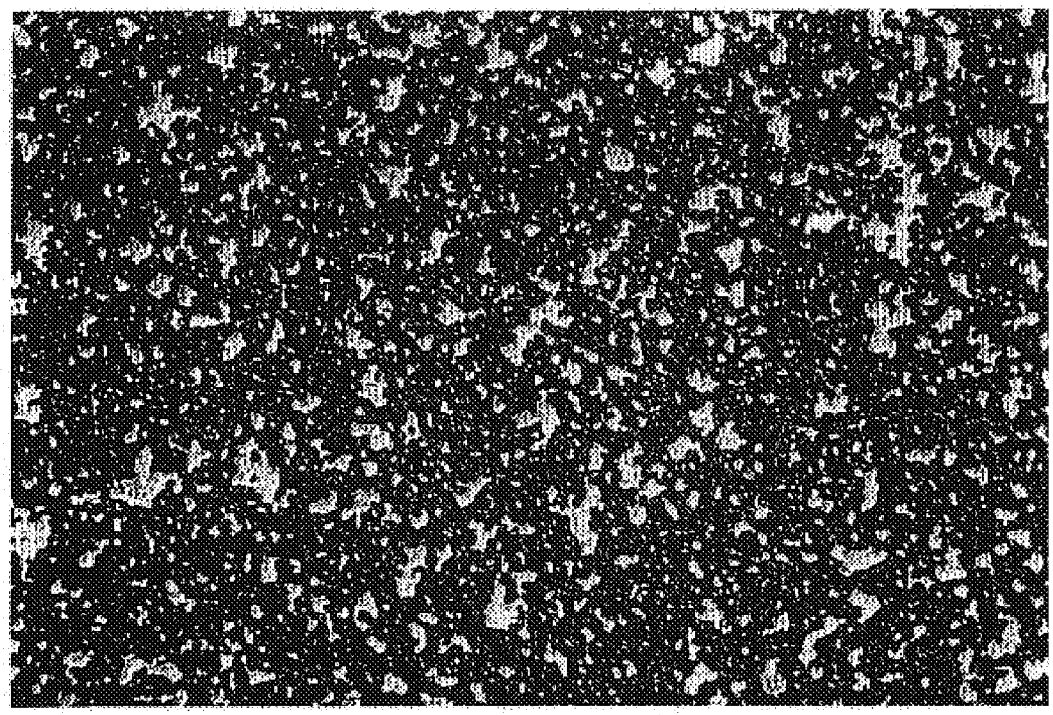
FIG. 7 shows a reflected light differential interference contrast micrograph of reticulated surface RET-004 using a 10× objective set for optimum contrast.
Figure 8:
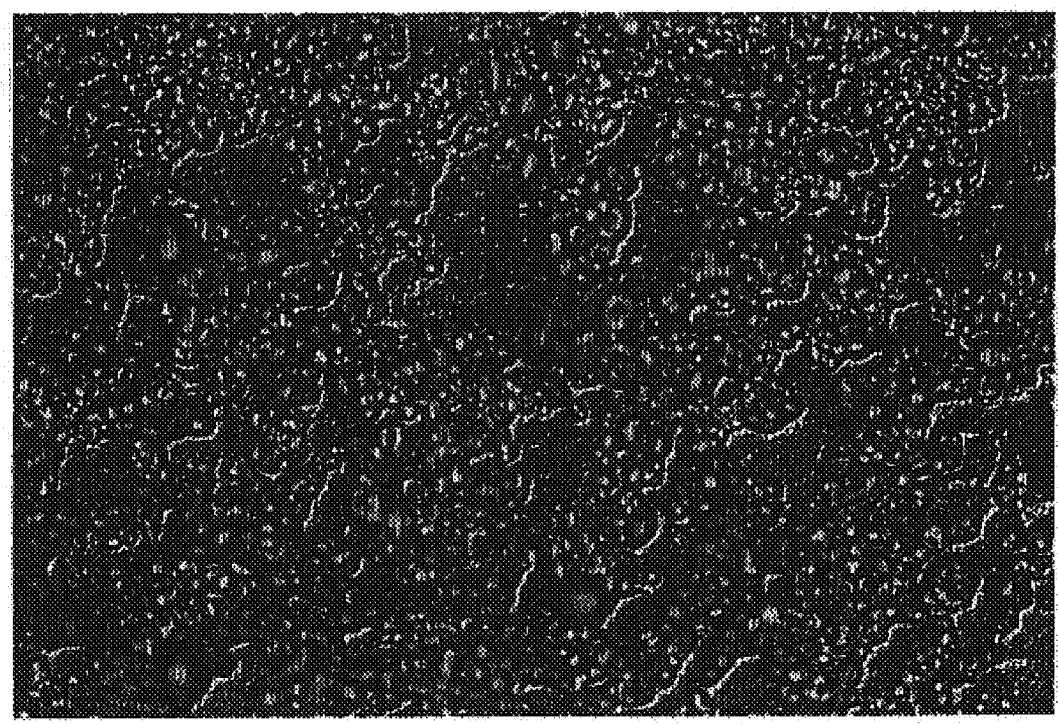
FIG. 8 shows a reflected light differential interference contrast micrograph of reticulated surface RET-004 using a 40× objective set for optimum contrast.
Figure 9:
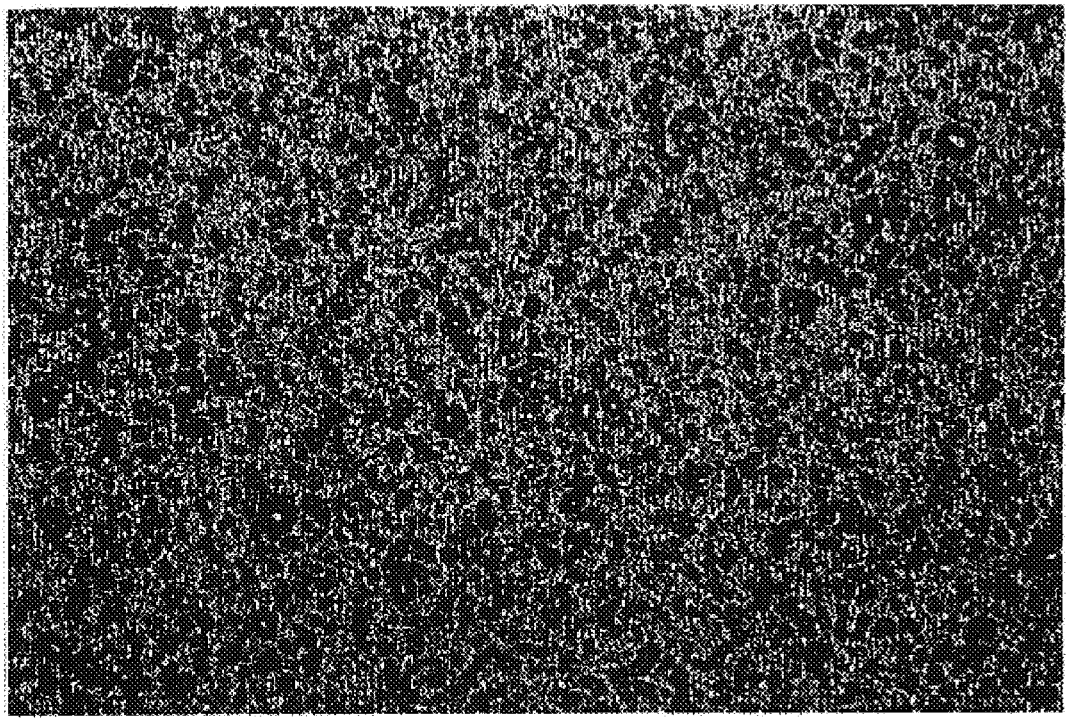
FIG. 9 shows a reflected light differential interference contrast micrograph of reticulated surface RET-005 using a 10× objective set for optimum contrast.
Figure 10:
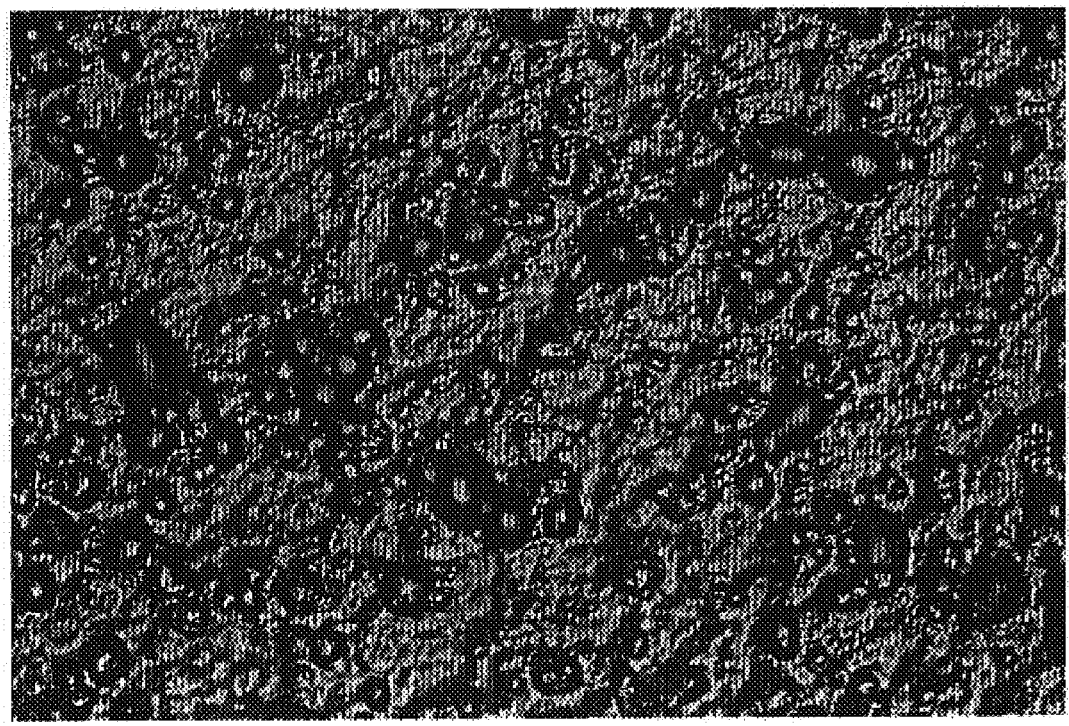
FIG. 10 shows a reflected light differential interference contrast micrograph of reticulated surface RET-005 using a 40× objective set for optimum contrast.

FIGS. 1–10 thus show reflected light differential interference contrast micrographs of reticulated surfaces (see RET-001 through RET-005 discussed in the foregoing) using either a 10× objective or a 40× objective set for optimum contrast. FIG. 1 shows a reflected light differential interference contrast micrograph of reticulated surface RET-001 using a 10× objective set for optimum contrast. FIG. 2 shows a reflected light differential interference contrast micrograph of reticulated surface RET-001 using a 40× objective set for optimum contrast. FIG. 3 shows a reflected light differential interference contrast micrograph of reticulated surface RET-002 using a 10× objective set for optimum contrast. FIG. 4 shows a reflected light differential interference contrast micrograph of reticulated surface RET-002 using a 40× objective set for optimum contrast. FIG. 5 shows a reflected light differential interference contrast micrograph of reticulated surface RET-003 using a 10× objective set for optimum contrast. FIG. 6 shows a reflected light differential interference contrast micrograph of reticulated surface RET-003 using a 40× objective set for optimum contrast. FIG. 7 shows a reflected light differential interference contrast micrograph of reticulated surface RET-004 using a 10× objective set for optimum contrast. FIG. 8 shows a reflected light differential interference contrast micrograph of reticulated surface RET-004 using a 40× objective set for optimum contrast. FIG. 9 shows a reflected light differential interference contrast micrograph of reticulated surface RET-005 using a 10× objective set for optimum contrast. FIG. 10 shows a reflected light differential interference contrast micrograph of reticulated surface RET-005 using a 40× objective set for optimum contrast.

Confocal Laser Scanning Microscopy (CLSM).

The use of CLSM gives information both on surface roughness and surface morphology. Because the technique is confocal, only that part of the image that is in focus is recorded. By adjusting the distance between the sample and the laser, changes in morphology with depth can be obtained. CLSM was performed on RET-003. Surface and sub-surface imaging was obtained using an uncoated sample. Gold coating of the surface enabled surface roughness measurements to be performed.

Roughness Measurements on a 282×190 $\mu$m region gave the following data:

| Measure | Value ($\mu$m) |
| --- | --- |
| $R_q$ (RMS) | 1.43 |
| $R_a$ | 1.03 |
| $R_{max}$ | 11.9 |

Environmental Scanning Electron Microscopy (ESEM) and Energy Dispersive X-ray (EDX) Analysis.

Typical environmental scanning electron micrographs obtained from RET-004 and 005 are shown in FIGS. 11 to 14 at 200× and 500× magnification, respectively. These show clearly the differences in morphology of the reticulated coatings between PVP and HEC and is in agreement with previous observations made at lower resolution by DIC microscopy.

Figure 11:
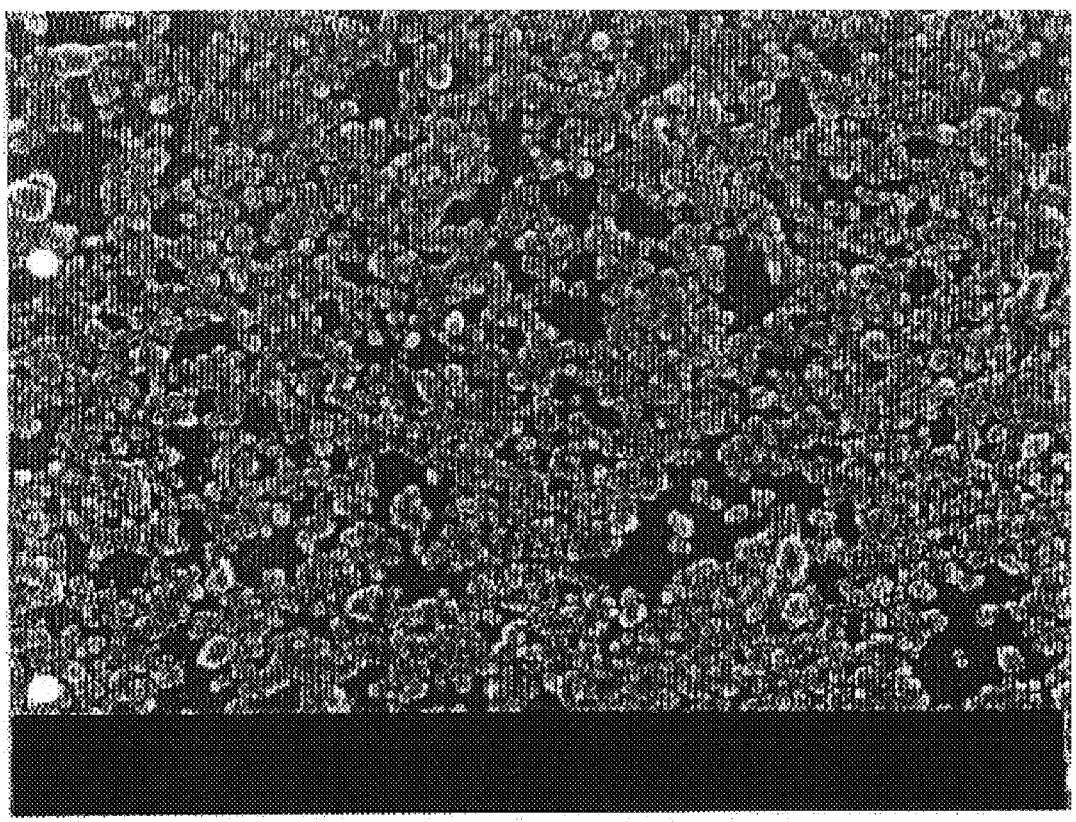
FIG. 11 shows an environmental scanning electron micrograph of reticulated surface RET-004 at 200× magnification.
Figure 12:
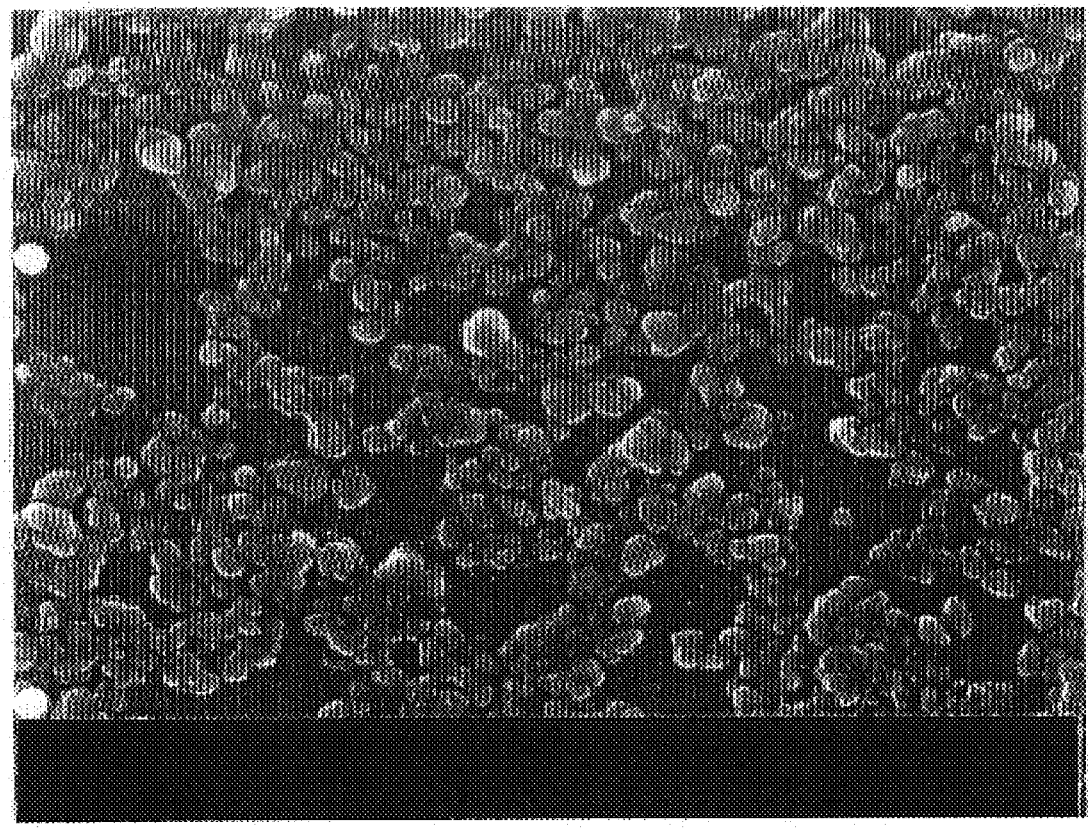
FIG. 12 shows an environmental scanning electron micrograph of reticulated surface RET-004 at 500× magnification.
Figure 13:
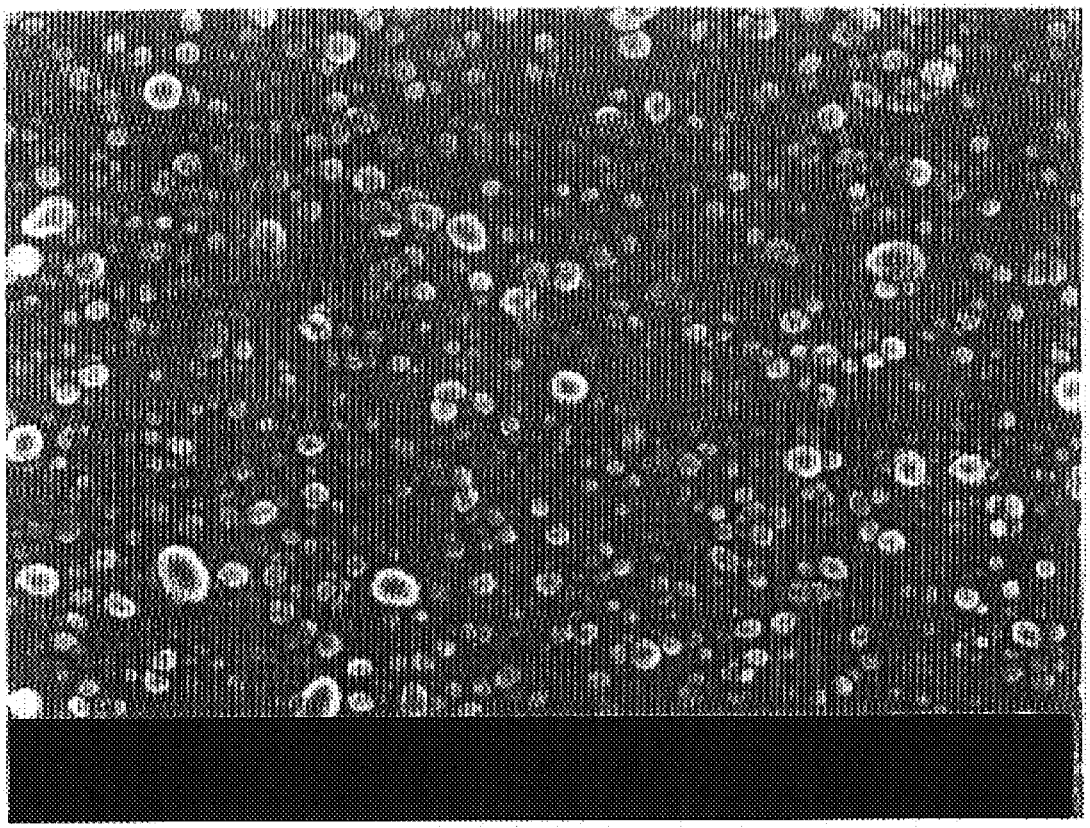
FIG. 13 shows an environmental scanning electron micrograph of reticulated surface RET-005 at 200× magnification.
Figure 14:
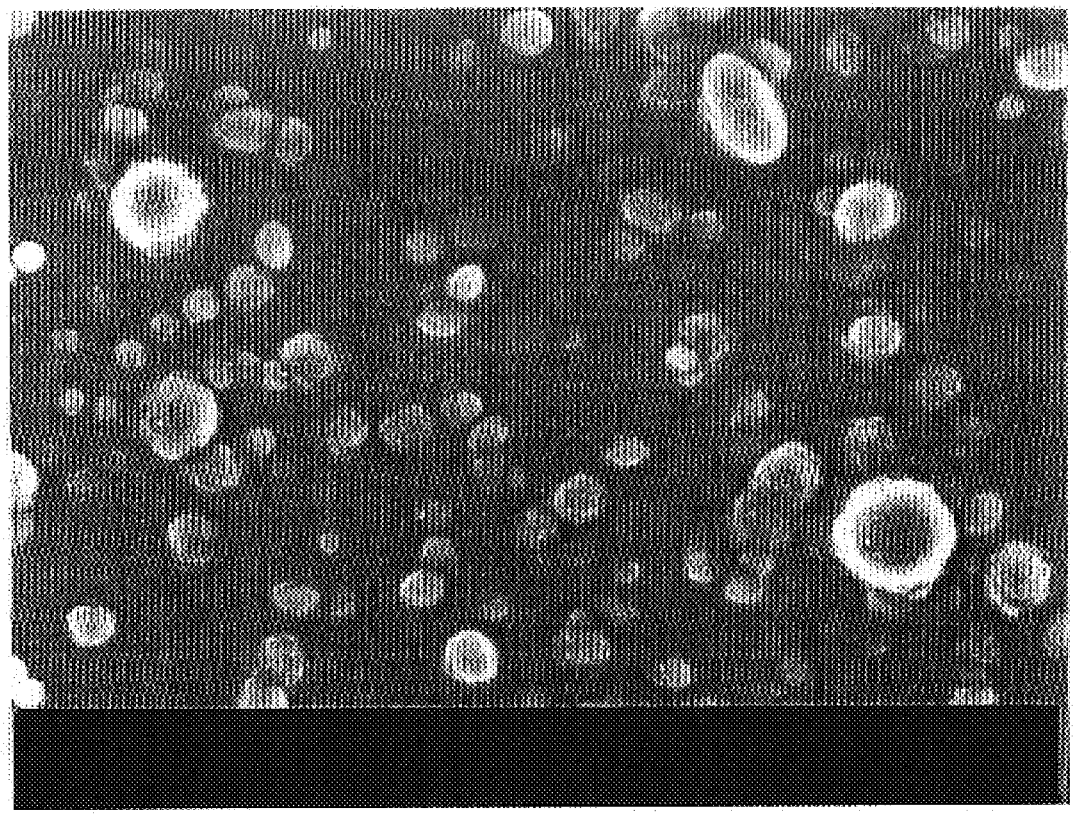
FIG. 14 shows an environmental scanning electron micrograph of reticulated surface RET-005 at 500× magnification.

FIGS. 11–14 thus show typical environmental scanning electron micrographs obtained from RET-004 and RET-005 (see RET-004 and RET-005 discussed in the foregoing) at 200× and 500× magnification. FIG. 11 shows an environmental scanning electron micrograph of reticulated surface RET-004 at 200× magnification. FIG. 12 shows an environmental scanning electron micrograph of reticulated surface RET-004 at 500× magnification. FIG. 13 shows an environmental scanning electron micrograph of reticulated surface RET-005 at 200× magnification. FIG. 14 shows an environmental scanning electron micrograph of reticulated surface RET-005 at 500× magnification.

Figure 15:
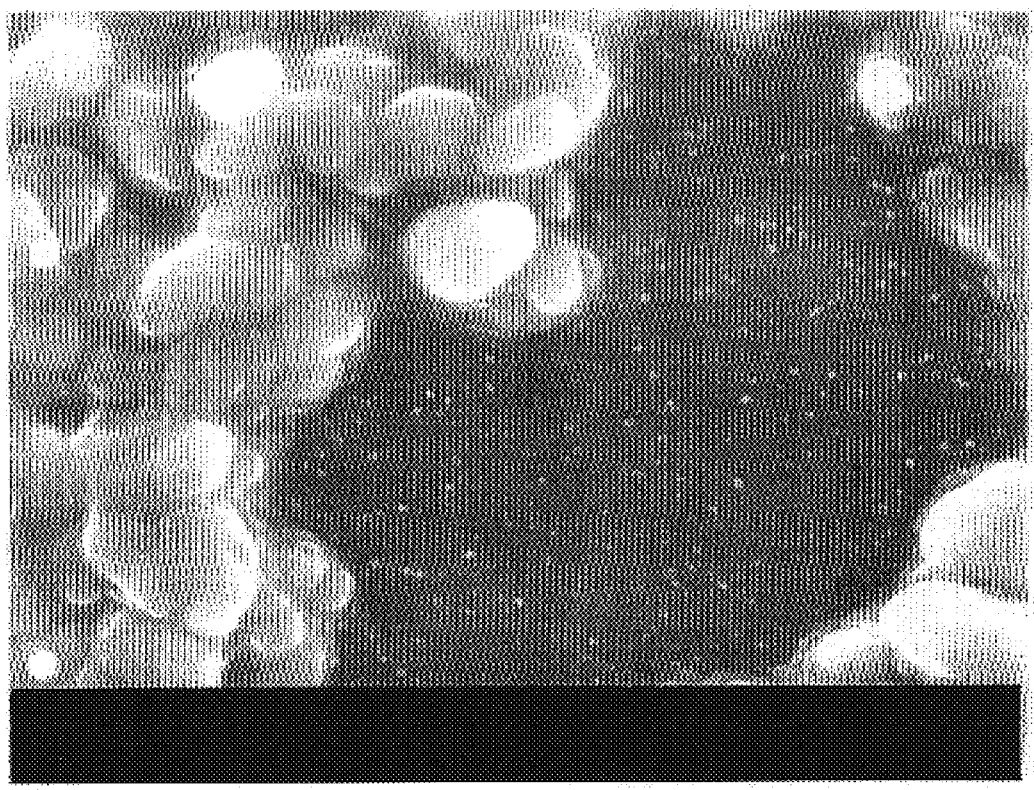
FIG. 15 shows an environmental scanning electron micrograph of reticulated surface RET-004 prior to final washing at 200× magnification.
Figure 16:
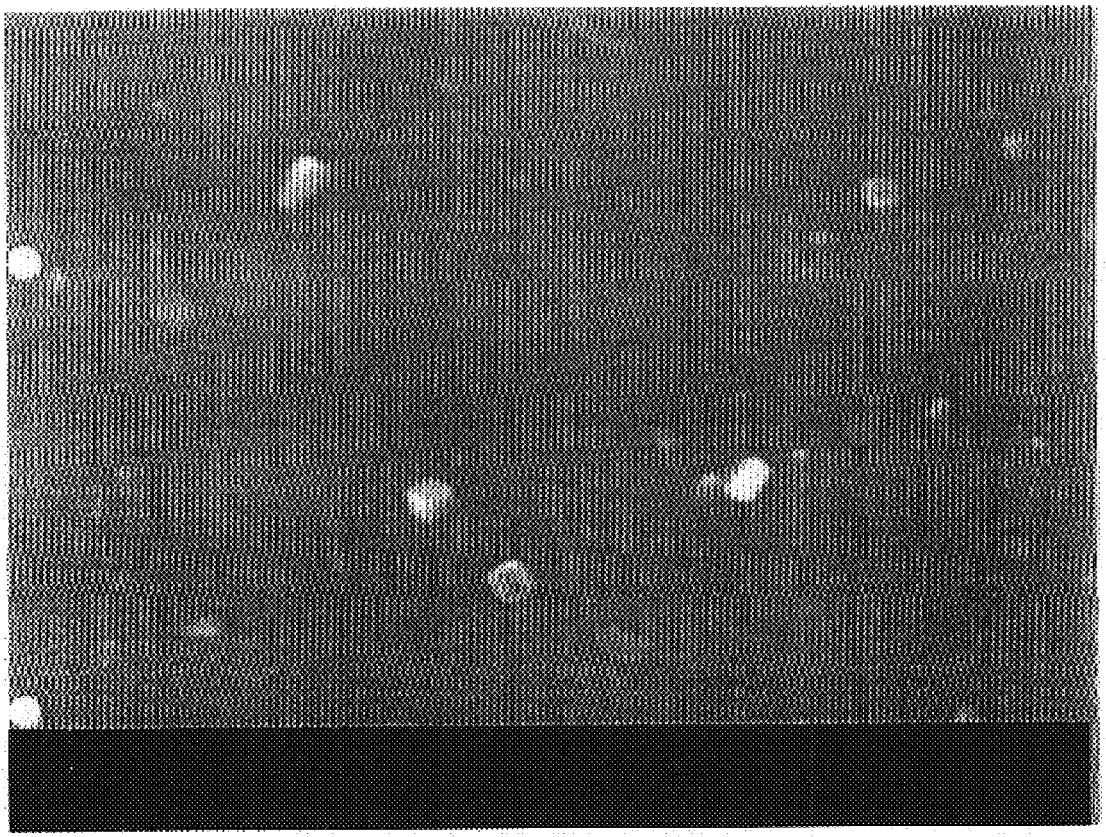
FIG. 16 shows an environmental scanning electron micrograph of reticulated surface RET-004 prior to final washing at 500× magnification.

ESEM of the reticulated surfaces was performed prior to final washing, in order to ascertain the relationship, if any, between sodium chloride precipitates and morphology. Typical ESEM pictures for RET-004 (PVP) are shown in FIGS. 15 and 16. Small sub-micron particles can be seen randomly distributed across the surface. Spot analysis revealed these to be sodium chloride. EDX analysis of the adjacent region revealed no sodium or chlorine bands. The sodium chloride precipitates only appear in the regions where there is no reticulated surface present, suggesting that the polyurethane has no affinity for the salt solution (as would be expected). In comparison, salt deposits on the RET-005 coating (HEC) appear to adhere to the surface of some of the reticulated particles, with fewer deposits being observed on the underlying substrate which suggests a difference in the properties of the two systems (see FIGS. 17 and 18). The differences in morphology between the two systems is more apparent. The individual particles of the PVP modified polymer have a smoother surface whilst the HEC coated polymer has a textured, granular morphology.

FIGS. 15 and 16 thus show environmental scanning electron micrographs obtained from RET-004 (PVP) prior to final washing. FIG. 15 shows an environmental scanning electron micrograph of reticulated surface RET-004 (PVP) prior to final washing at 200× magnification. FIG. 16 shows an environmental scanning electron micrograph of reticulated surface RET-004 (PVP) prior to final washing at 500× magnification.

Figure 17:
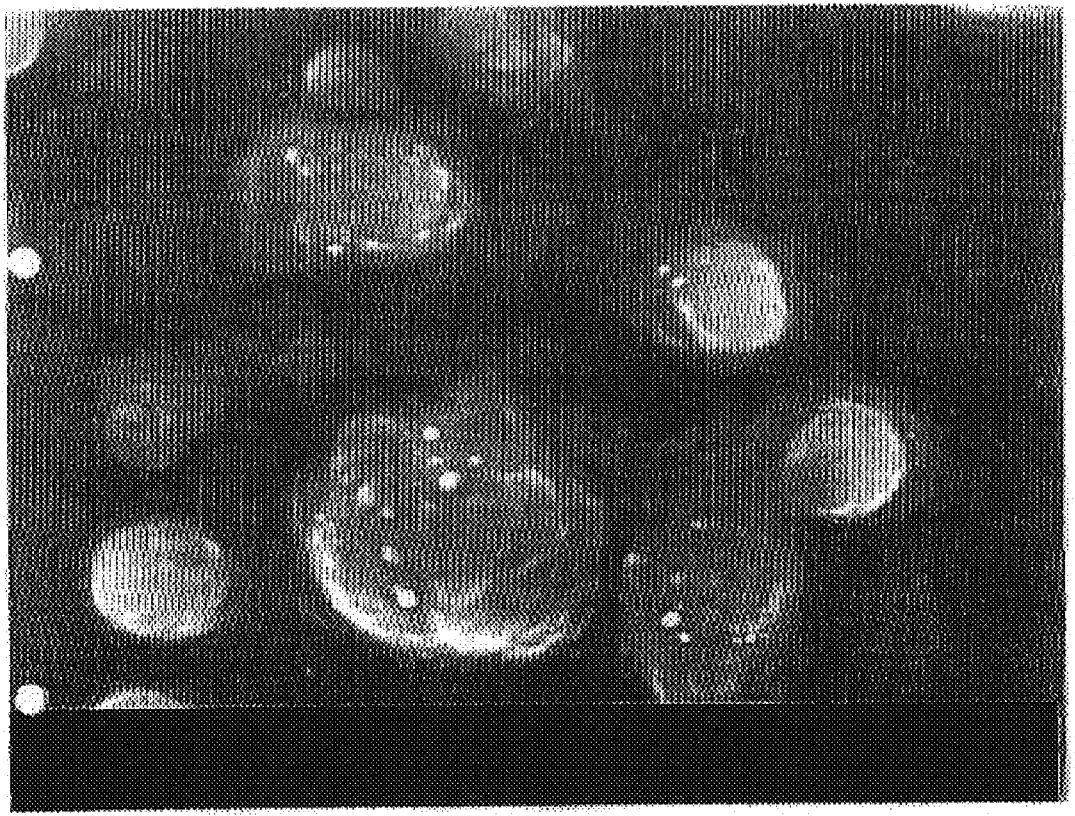
FIG. 17 shows an environmental scanning electron micrograph of reticulated surface RET-005 prior to final washing at 200× magnification.
Figure 18:
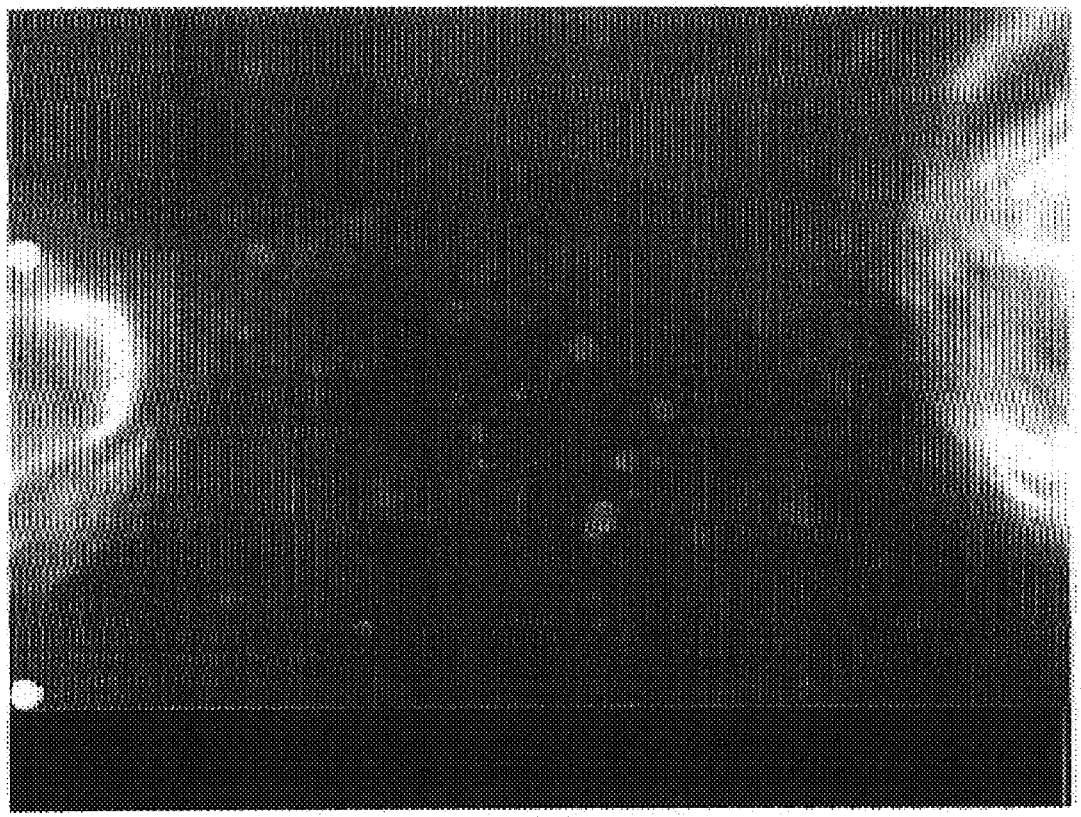
FIG. 18 shows an environmental scanning electron micrograph of reticulated surface RET-005 prior to final washing at 500× magnification.

FIGS. 17 and 18 show environmental scanning electron micrographs obtained from RET-005 (HEC) prior to final washing. FIG. 17 shows an environmental scanning electron micrograph of reticulated surface RET-005 (HEC) prior to final washing at 200× magnification. FIG. 18 shows an environmental scanning electron micrograph of reticulated surface RET-005 prior to final washing at 500× magnification.

Atomic Force Microscopy (AFM).

Increasing the resolution further, AFM was performed on RET-003 using a Digilab® instrument in the tapping mode. This mode of operation utilises a high frequency vertical displacement in order to prevent adhesion of the probe tip to the substrate. This is particularly important when attempting to obtain AFM images from soft elastomeric substrates. Analysis of the surface roughness of a typical region of the reticulated surface by AFM gave the following data:

| Measure | Value (nm) |
|---|---|
| $R_q$ (RMS) | 111.6 |
| $R_a$ | 79.6 |
| $R_{max}$ | 768.5 |

Taking the background area (i.e., excluding the reticulated region) gives the following:

| Measure | Value (nm) |
|---|---|
| $R_q$ (RMS) | 34.5 |
| $R_a$ | 20.6 |
| $R_{max}$ | 188.7 |

It is noted that the surface roughness values obtained by AFM are less than those obtained by CSLM. This is probably due to averaging over a smaller sample area. The underlying surface texture is one of a very smooth uniform polymer.

Transmission Electron Microscopy (TEM) Analysis of the Particle Size Distribution.

In an attempt to understand the role of the micelle structure in the formation of the reticulated surface, the true particle size and particle size distribution has been measured using TEM analysis. A 10% solution was dispersed onto a holey carbon grid. TEM pictures of the two dispersed polymers (Sancure® 2255 and base polymer) were taken at 40, 100 and 200kx magnification, followed by image analysis. Results (see FIGS. 19 and 20) are presented based on a 1000 particle count and show that the micelles of the two polymers (Sancure® 2255 and base polymer) exhibit similar particle sizes (38 and 34 nm, respectively). Electron micrographs show that the micelles are lenticullar in shape with an internal structure. No significant differences can be observed between the two polymer systems.

Figure 19:
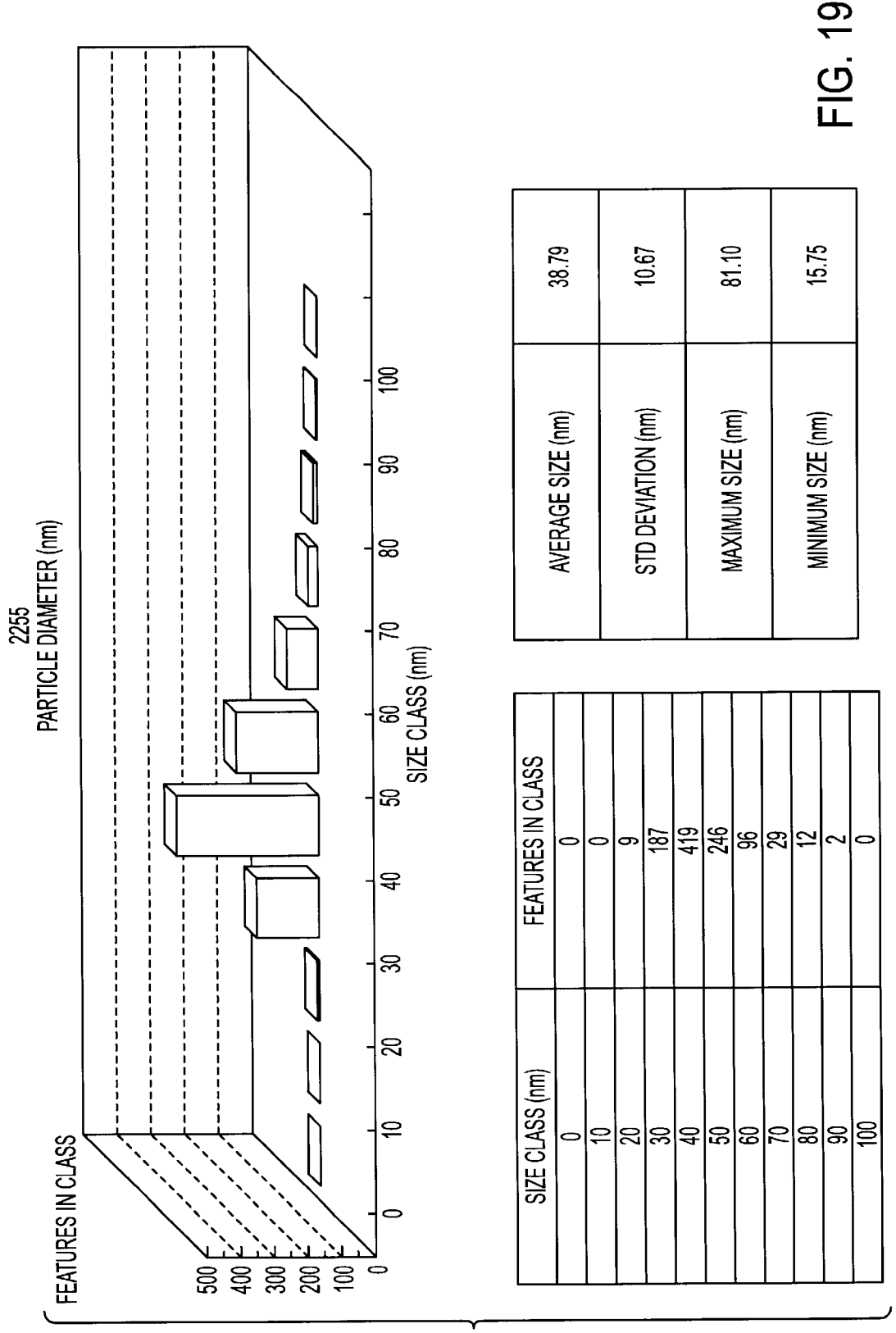
FIG. 19 shows the results of an image analysis of a transmission electron micrograph of a 10% dispersion of Sancure® 2255 polymer based on 1000 particle count.
Figure 20:
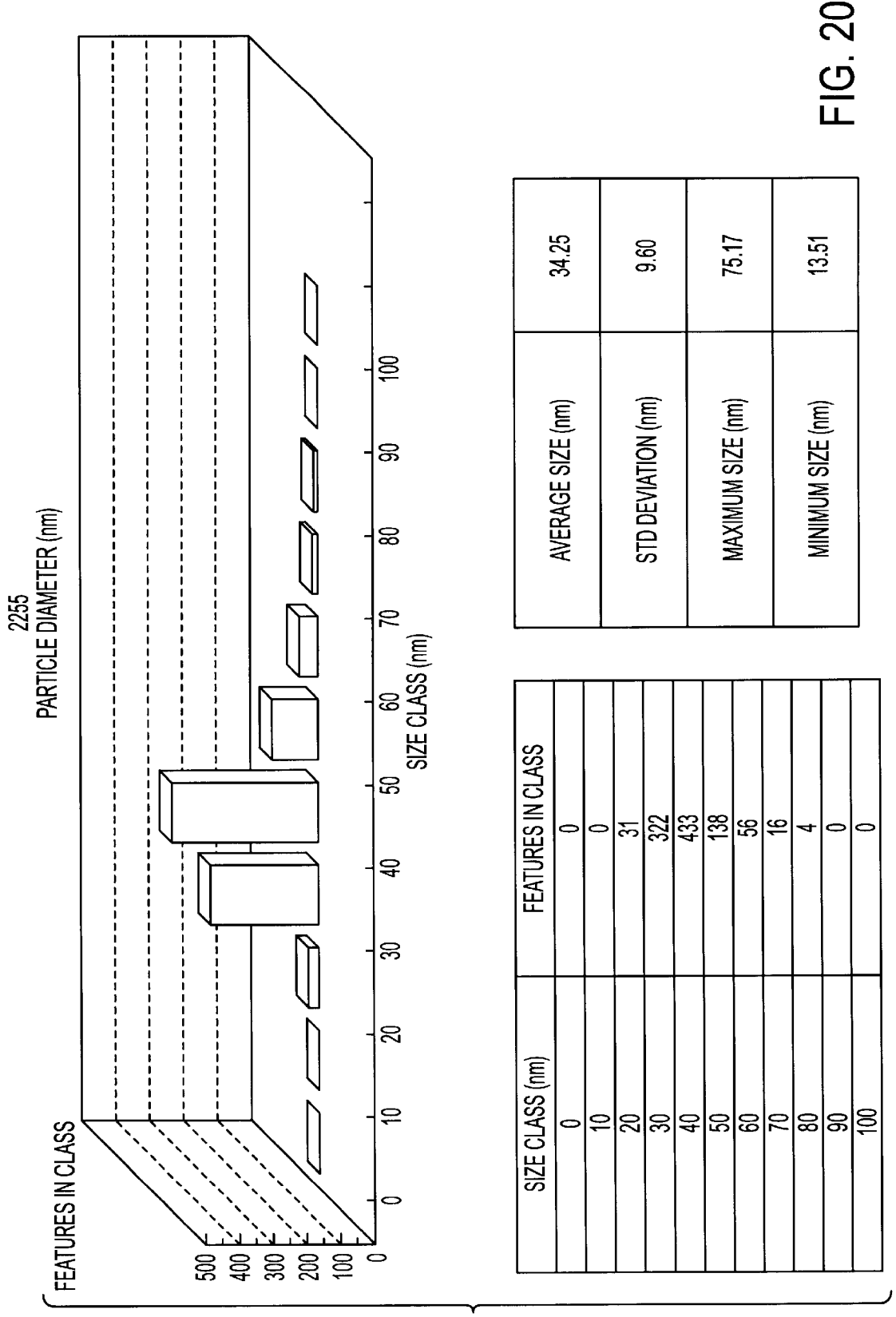
FIG. 20 shows the results of an image analysis of a transmission electron micrograph of a 10% dispersion of base polymer based on a 1000 particle count.

FIG. 19 shows the results of an image analysis of a transmission electron micrograph of a 10% dispersion of Sancure® 2255 polymer based on 1000 particle count. FIG. 20 shows the results of an image analysis of a transmission electron micrograph of a 10% dispersion of base polymer based on a 1000 particle count. A comparison of FIGS. 19 and 20 show that no significant differences were observed between the two polymer systems regarding the micelle structure's role in the formation of the reticulated surfaces.

Fourier Transform Infrared (FTIR) Spectroscopy.

FTIR-ATR microscopy (obtained at 100 $\mu$m resolution) has been performed on the polymers (Sancure® 2255 & base polymer) as well as PVP, HEC and the reticulated coatings applied to base polymer substrate. A comparison of the two polyurethane spectra show only subtle differences between them (e.g. bands between 1100 and 1000 cm$^{-1}$), but sufficient to tell the two polymers apart. The reference spectra of PVP and HEC show that they can be easily differentiated from the polyurethane by bands at 1643 cm$^{-1}$, etc. for PVP and 1050 cm$^{-1}$ for HEC. The spectra obtained for the PVP addition to Sancure® 2255 show that the reticulated region differs spectroscopically from the non-reticulated region. By subtraction spectroscopy it can be shown that both regions contain a certain proportion of PVP. The reticulated region contains Sancure® 2255 polyurethane whilst the non-reticulated region contains base polymer (as would be expected). There is evidence of weak interaction (hydrogen bonding) between the PVP and the two polyurethanes. This is evidenced by the band previously observed at 1643 cm$^{-1}$ (assigned to C=O stretching) shifting 16 cm$^{-1}$ to 1659 cm$^{-1}$. Additional evidence (not shown) of hydrogen bonding occurring is to be found in the —OH stretching region. In the spectra obtained for the addition of HEC to Sancure® 2255, no evidence can be found in the reticulated or non-reticulated region for the presence of HEC. The spectra of the reticulated region is purely that of Sancure® 2255. Clearly in this system there is no interaction occurring with the urethanes, i.e., they are either incompatible or immiscible with HEC. This is in contrast to the addition of PVP to polyurethane where some degree of compatibility exists. The structure and morphology of the reticulated coating can be controlled through processing conditions and composition. The key parameters are the miscibility between the components, the ion concentration in solution, and the temperature and time given to drying the polyurethane base coat prior to applying the reticulated coating. Less important but still relevant is the type of substrate used. Other parameters such as pH, molecular weight of the second phase (e.g., PVP) and the type of ion used (e.g., the use of zinc, calcium, lithium, etc. may have an effect) may also have an influence.

EXAMPLE 2

Procedure for Providing a Polyurethane Condom With a Reticulated Coating 1 liter of coating mixture was prepared by dispersing 16 g of polyvinylpyrrolidone (PVP, average MW 1,300,000, available from Aldrich Chemicals, Gillingham, UK) and 6 g of NaCl in 636 g of de-ionized water. Once the solids were fully dispersed, 342 g of Sancure® 2255 (an aqueous polyurethane dispersion available from B F Goodrich, Leominister, Mass., USA) was added to the NaCl/PVP solution with the mixture being constantly agitated. The mixture was agitated for a further 12 hours before the coating procedure commenced.

A glass condom dipping former of traditional design was coated with polyurethane by immersing it into a container of Sancure® 20003 at an inward speed of 20 mm/sec (0.8 in/sec) and withdrawing it from the solution using a withdrawal speed of 3 mm/sec (0.12 in/sec). The coated former was then heated for 5 minutes at 80° C. (176° F.). The former was then immersed into the PVP/NaCl/Polyurethane coating mixture to the level of the first coating using an immersion speed of 20 mm/sec (0.8 in/sec), while maintaining continual gentle agitation of the coating mixture. The dipping former was then dried at 80° C. (176° F.) for 25 minutes. The former was then immersed in a bath of de-ionized water for a period of 5 minutes and the coated condom was then manually stripped from the former. The coated polyurethane condom was dried in a warm air-stream.

This procedure may be used to provide a latex condom with a reticulated coating, although the latex coated former may optionally be dipped into a solution of a suitable tie-coating material first, to improve adherence of the reticulated coating. Similar procedures may also be used for providing reticulated coatings on other dip-formed articles, such as examination gloves, surgical gloves, angioplasty balloons and the like.

Figure 21:
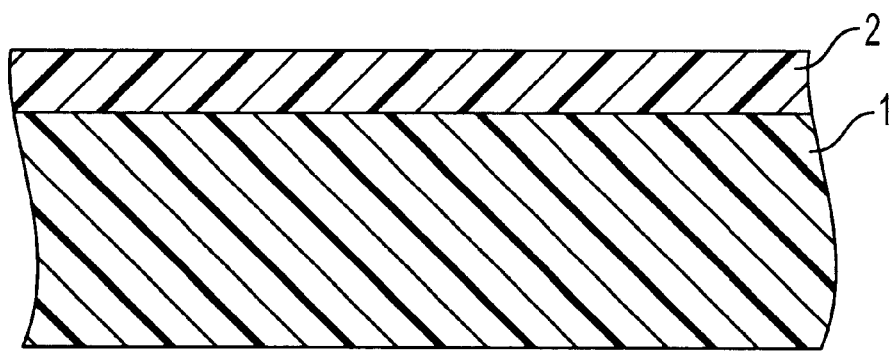
FIG. 21 schematically shows in partial cross-section a reticulated coating 2 according to the invention provided on a substrate 1 which may be an article including a condom, a medical glove, a wound dressing, a catheter, an angioplasty balloon, a stent, a valve, or a surgical suture.

FIG. 21 shows in partial cross-section a substrate 1 provided with a reticulated coating 2 according to the invention which may be an article including a condom, a medical glove, a wound dressing, a catheter, an angioplasty balloon, a stent, a valve, or a surgical suture.

It should be understood, however, that the invention is not limited to the foregoing examples and that many other reticulated coatings prepared in accordance with the invention and their use in many different applications will be readily apparent to those skilled in the art from the preceding detailed description.

What is claimed is:

1. A method of forming a reticulated coating on a substrate, comprising:
    forming an agglomerate dispersion of a pre-formed first polymer in a polar liquid carriers;
    applying the agglomerate dispersion to the surface of the substrate; and
    evaporating the polar liquid carrier to form the reticulated coating.

2. A method as claimed in claim 1, wherein the reticulated coating is adapted to render the surface of the substrate substantially tack-free or anti-blocking when dry.

3. A method as claimed in claim 1, wherein the reticulated coating is substantially free of substances capable of causing undesirable allergic hypersensitivity reactions.

4. A method as claimed in claim 1, wherein the reticulated coating has a minimum Ra value of at least 0.5 $\mu$m.

5. A method as claimed in claim 4, wherein the reticulated coating has an Ra value in the range of 0.5–100 $\mu$m, preferably 1–50 $\mu$m, more preferably, 2–25 $\mu$m and most preferably about 5 $\mu$m.

6. A method as claimed in claim 1, wherein the reticulated coating is also lubricious, preferably having a low coefficient of friction when wet or dry.

7. A method as claimed in claim 1, wherein the agglomerate dispersion is applied to the surface of the substrate by spraying or dipping.

8. A method as claimed in claim 1, wherein the agglomerate dispersion is formed from a colloidal dispersion of the first polymer.

9. A method as claimed in claim 8, wherein the colloidal dispersion is an aqueous dispersion containing micelles of the first polymer component having an average particle size in the range of 0.1–100 nm, preferably 1–75 nm, and most preferably about 50 nm.

10. A method as claimed in claim 1, wherein the agglomerate dispersion is formed in the presence of an electrolyte, preferably a metal salt or an ammonium salt.

11. A method as claimed in claim 10, wherein the agglomerate dispersion is formed by vigorous agitation of a mixture of the first polymer and the polar liquid carrier in the presence of a surfactant and/or an electrolyte.

12. A method as claimed in claim 1, wherein the agglomerate dispersion is formed in the presence of a surfactant.

13. A method as claimed in claim 1, wherein the average size of the particles in the agglomerate dispersion is in the range of 0.1–100 $\mu$m, preferably 0.5–25 $\mu$m, and most preferably 1–15 $\mu$m.

14. A method as claimed in claim 1, wherein the agglomerated particles of the first polymer are substantially evenly dispersed in the polar liquid carrier.

15. A method as claimed in any one of the preceding claims, wherein the first polymer is capable of forming a substantially stable solution with the polar liquid carrier.

16. A method as claimed in claim 15, wherein the substantially stable solution is a colloidal solution.

17. A method as claimed in claim 15, wherein the first polymer is capable of forming micelles in the polar liquid carrier, ideally having an average particle size in the range of 0.1–100 nm, preferably 1–75 nm, and most preferably about 50 nm.

18. A method as claimed in claim 1, wherein the first polymer comprises a thermoplastic, a thermosetting resin or an elastomer, preferably a polyurethane or a natural rubber.

19. A method as claimed in claim 1, wherein the polar liquid carrier is an aqueous liquid.

20. A method as claimed in claim 1, wherein the surface of the substrate is substantially smooth or non-reticulated, prior to application of the coating.

21. A method as claimed in claim 20, wherein the surface of the substrate has an Ra value of less than 0.5 $\mu$m.

22. A method as claimed in claim 21, wherein the agglomerate dispersion further comprises a second polymer.

23. A method as claimed in claim 22, wherein the second polymer is capable of interacting with the polar liquid carrier in such a way that the first polymer is induced to form an agglomerate dispersion in the polar liquid carrier.

24. A method as claimed in claim 23, wherein the second polymer forms an intimate network with the polar liquid carrier, thereby reducing the ability of the polar liquid carrier to interact with the first polymer and causing the first polymer to form an agglomerate dispersion in the polar liquid carrier.

25. A method as claimed in claim 22, wherein the second polymer has at least one polar group capable of interacting with the polar liquid carrier.

26. A method as claimed in claim 25, wherein the second polymer has a plurality of polar groups capable of solvation by the polar liquid carrier.

27. A method as claimed in claim 26, wherein the polar liquid carrier solvates or forms solvation spheres with the second polymer in preference to the first polymer, thereby causing the first polymer to form an agglomerate dispersion in the polar liquid carrier.

28. A method as claimed in claim 27, wherein the first polymer is initially present in the form of micelles and the second polymer causes the micelles to aggregate, thereby forming an agglomerate dispersion of the first polymer in the polar liquid carrier.

29. A method as claimed in any one of claim 22, wherein the polar liquid carrier is aqueous and is capable of hydrogen bonding with polar groups on the second polymer, such that the ability of the polar liquid carrier to hydrogen bond with polar groups on micelles of the first polymer is reduced, thereby causing the micelles to aggregate.

30. A method as claimed in any one of claim 22, wherein the second polymer is selected from the group consisting of polystyrene, polymethyl methacrylate, polyvinylpyrrolidone, poly(N-vinyl caprolactam), hydroxymethylcellulose, hydroxyethylcellulose and mixtures thereof.

31. A method as claimed in claim 1, further comprising the step of washing the coated substrate to remove unwanted residues.

32. A method as claimed in claim 31, wherein the agglomerate dispersion comprises a second polymer and the washing step removes substantially all of the second polymer from the coating.

33. A method as claimed in claim 32, wherein the second polymer comprises hydroxyethylcellulose.

34. A method as claimed in claim 31, wherein the agglomerate dispersion comprises a second polymer and the second polymer is substantially undissolved by the washing step, remaining present in the coating.

35. A method as claimed in claim 34, wherein the second polymer comprises polyvinylpyrrolidone.

36. A method as claimed in claim 1, further comprising the step of applying a third polymer to the surface of the substrate, prior to providing the surface with the agglomerate dispersion of the first polymer.

37. A method as claimed in claim 36, wherein the third polymer forms a tie-coating, to improve adherence of the agglomerate dispersion.

38. A method as claimed in claim 36, wherein the first and the third polymers comprise the same thermoplastic, thermosetting resin or elastomer, preferably a polyurethane or a natural rubber.

39. A method as claimed in claim 36, wherein the third polymer is applied to the surface of the substrate in solution or suspension.

40. A method as claimed in claim 39, wherein the surface of the substrate is dried before being provided with the agglomerate dispersion.

41. A method as claimed in claim 40, wherein the surface of the substrate is dried at a temperature of 15–150° C. for a period of 1–60 minutes, preferably at 50–100° C. for 1–30 minutes, and most preferably at about 80° C. for about 5–10 minutes.

42. A method as claimed in claim 1, further comprising the step of applying a surfactant to the coated surface of the substrate, preferably one comprising a silicone or an organosiloxane polymer.

43. A reticulated coating obtainable by a method as claimed in claim 1.

44. A method of preparing a film article having a reticulated coating, which comprises the steps of providing a dipping former of the article, dipping the former into a solution of a polymeric material to form the film article, and forming a reticulated coating on a surface of the film article by a method as claimed in claim 1.

45. A method as claimed in claim 44, wherein the film article is a condom or a glove.

46. A film article obtainable by a method as claimed in claim 44.

47. An article having a reticulated coating formed by providing an agglomerate dispersion of a pre-formed first polymer in a polar liquid carrier on a surface of the substrate, and evaporating the liquid carrier to form the coating.

48. An article as claimed in claim 47, wherein the coating has a reticulated component particle size of 1–25 $\mu$m and an $R_a$ value of 1–10 $\mu$m, preferably a reticulated component particle size of 2–12 $\mu$m and an $R_a$ value of about 5 $\mu$m.

49. An article as claimed in claim 47, being a condom, a medical glove, a wound dressing, a cathether, an angioplasty balloon, a stent, a valve, or a surgical suture.

50. A condom or a medical glove having a reticulated coating formed from an agglomerate dispersion of polyurethane and polyvinylpyrrolidone, or polyurethane and hydroxyethylcellulose, in aqueous solution.

* * * * *